(12) United States Patent  (10) Patent No.: US 8,062,368 B2
Heinz et al.  (45) Date of Patent: Nov. 22, 2011

(54) EXPANDABLE VERTEBRAL IMPLANTS AND METHODS OF USE

(75) Inventors: Eric Steven Heinz, Mountain View, CA (US); William Sears, Warrawee (AU)

(73) Assignee: Warsaw Orthopedic, Inc., Warsaw, IN (US)

( * ) Notice: Subject to any disclaimer, the term of this patent is extended or adjusted under 35 U.S.C. 154(b) by 697 days.

(21) Appl. No.: 12/108,749

(22) Filed: Apr. 24, 2008

(65) Prior Publication Data

US 2009/0270987 A1  Oct. 29, 2009

(51) Int. Cl.
   *A61F 2/44* (2006.01)
(52) U.S. Cl. .................................................. 623/17.11
(58) Field of Classification Search ..... 623/17.11–17.16
   See application file for complete search history.

(56) References Cited

U.S. PATENT DOCUMENTS

| | | | |
|---|---|---|---|
| 4,932,975 A | 6/1990 | Main et al. | |
| 5,549,679 A | 8/1996 | Kuslich | |
| 6,582,467 B1 | 6/2003 | Teitelbaum et al. | |
| 6,749,614 B2 | 6/2004 | Teitelbaum et al. | |
| 6,821,277 B2 | 11/2004 | Teitelbaum | |
| 6,875,212 B2 | 4/2005 | Shaolian et al. | |
| 6,899,713 B2 | 5/2005 | Shaolian et al. | |
| 6,964,667 B2 | 11/2005 | Shaolian et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0198526 A1 | 12/2002 | Shaolian et al. | |
| 2004/0006341 A1 | 1/2004 | Shaolian et al. | |
| 2004/0082954 A1 | 4/2004 | Teitelbaum et al. | |
| 2004/0087950 A1 | 5/2004 | Teitelbaum | |
| 2004/0199252 A1 | 10/2004 | Sears et al. | |
| 2004/0215193 A1 | 10/2004 | Shaolian et al. | |
| 2004/0230309 A1 | 11/2004 | DiMauro et al. | |
| 2005/0096746 A1 | 5/2005 | Bryan et al. | |
| 2005/0149022 A1 | 7/2005 | Shaolian et al. | |
| 2005/0234453 A1 | 10/2005 | Shaolian et al. | |
| 2005/0256576 A1 | 11/2005 | Moskowitz et al. | |
| 2005/0261769 A1 | 11/2005 | Moskowitz et al. | |
| 2007/0032875 A1* | 2/2007 | Blacklock et al. | 623/17.15 |
| 2010/0087924 A1* | 4/2010 | Arlet | 623/17.12 |

* cited by examiner

*Primary Examiner* — Eduardo C Robert
*Assistant Examiner* — Summer Kostelnik

(57) ABSTRACT

Illustrative embodiments disclosed herein are directed to vertebral implants and methods of use. In one embodiment, the implant includes first and second end members with an intermediate cage. The cage may be inflatable such that the implant is positionable between a collapsed state with a first reduced height to facilitate insertion between the first and second vertebral members, and an extended state with a second height greater than the first height that positions the first end member against the first vertebral member and the second end member against the second vertebral member to maintain an intervertebral axial space.

19 Claims, 8 Drawing Sheets

EXPANDABLE VERTEBRAL IMPLANTS AND METHODS OF USE

BACKGROUND

Spinal implants are often used in the surgical treatment of spinal disorders such as degenerative disc disease, disc herniations, scoliosis or other curvature abnormalities, and fractures. Many different types of treatments are used, including the removal of one or more vertebral bodies and/or intervertebral disc tissue. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies.

Regardless of the type of treatment and the type of implant used, surgical implantation tends to be a difficult for several reasons. For instance, access to the affected area may be limited by other anatomy. Further, a surgeon must be mindful of the spinal cord and neighboring nerve system. The size of the implant may present an additional obstacle. In some cases, a surgeon may discover that an implanted device has an inappropriate size for a particular application, which may require removal of the implant and insertion of a different implant. This trial and error approach may increase the opportunity for injury and is certainly time-consuming. Expandable implants are becoming more prevalent as a response to some of these concerns. However, the expansion mechanism in these devices tends to be complex and large. Consequently, existing devices do not appear to address each of these issues in a manner that improves the ease with which the device may be surgically implanted.

SUMMARY

Illustrative embodiments disclosed herein are directed to vertebral implants and methods of use. In one embodiment, the implant includes first and second end members with an intermediate cage. The cage may be inflatable such that it is positionable between a collapsed state with a first reduced height to facilitate insertion between the first and second vertebral members, and an extended state with a second height greater than the first height that positions the first end member against the first vertebral member and the second end member against the second vertebral member to maintain an intervertebral axial space.

DETAILED DESCRIPTION

Figure 1:
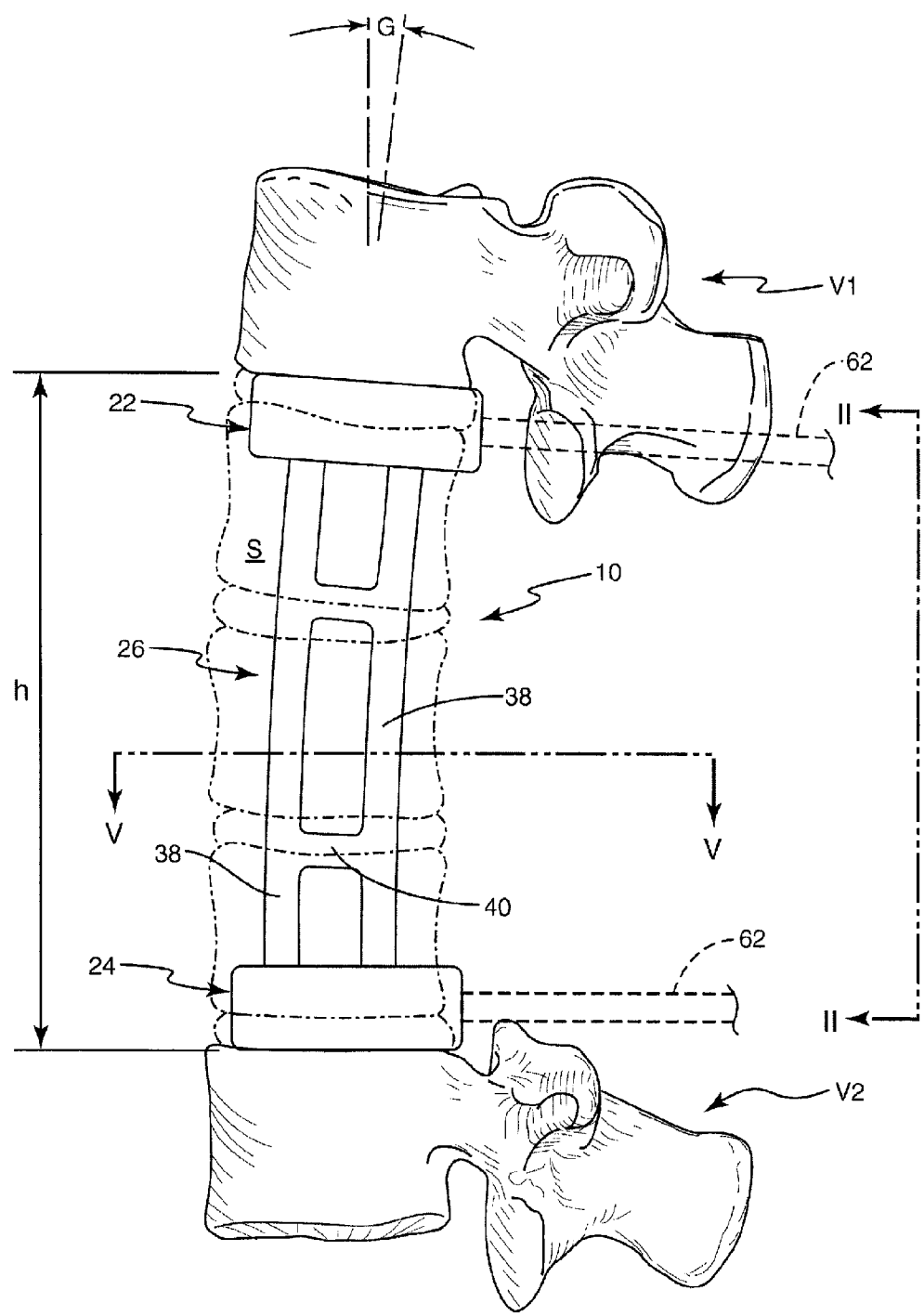
FIG. 1 is a side elevation view of a vertebral implant according to one embodiment positioned between vertebral bodies.

The various embodiments disclosed herein are directed to vertebral implants that are characterized by at least one expandable portion. The expandable portion may be compressed or left unfilled during installation of the implant and may be filled with an injectable substance once the implant is positioned within the body. An exemplary implant 10 for supporting vertebral bodies is illustrated in FIG. 1. In one embodiment, the implant 10 is a vertebrectomy cage assembly positionable within an intervertebral space to span one or more vertebral levels along the longitudinal axis of the spinal column. Although the illustrated embodiment of the implant 10 spans three vertebral levels, it should be understood that the implant 10 may be configured to span a single vertebral level, two vertebral levels, or four or more vertebral levels.

The implant 10 generally includes a first end member 22, a second end member 24, and one or more expandable portions 26 coupled between the first and second end members 22, 24. In one embodiment, the end members 22, 24 are formed of a radiolucent material, such as, for example, a carbon fiber material, or non-metallic substances, including polymers or copolymers made from materials such as PEEK and UHMWPE. In this manner, x-ray viewing of the intervertebral space S and the vertebral endplates subsequent to implantation of the implant 10 will be relatively unobstructed. In further embodiments, the end members 22, 24 may be formed of other suitable biocompatible materials, such as, for example, stainless steel, titanium, cobalt-chrome, and shape memory alloys.

Figure 2A:
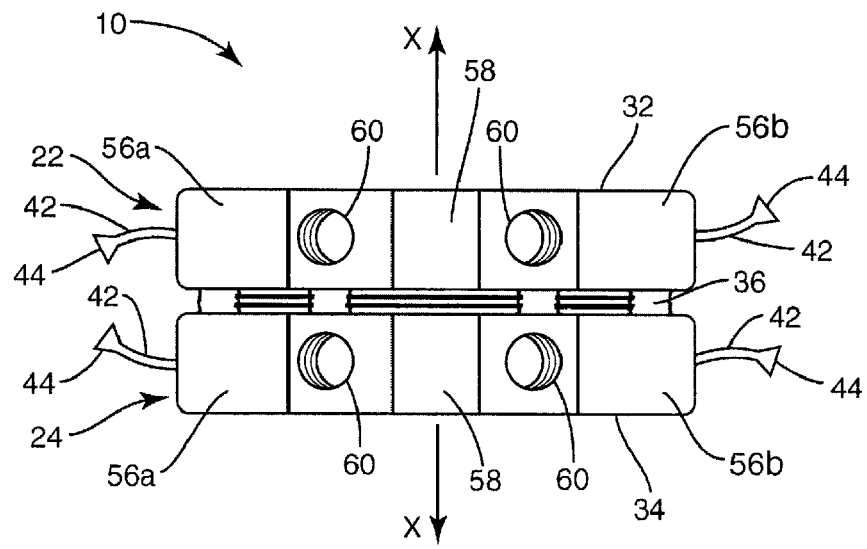
FIG. 2A is a posterior view of one embodiment of a vertebral implant in a collapsed state.
Figure 2B:
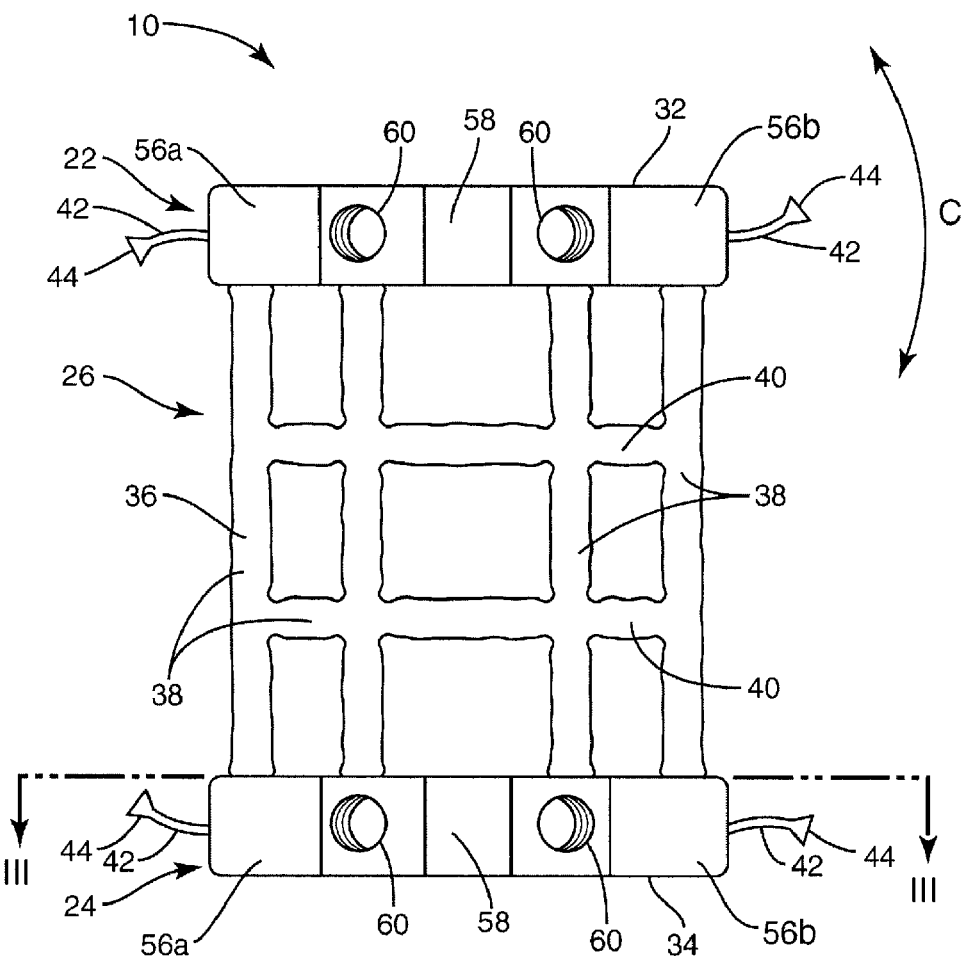
FIG. 2B is a posterior view of one embodiment of a vertebral implant in an extended state.

The end members 22, 24 are adapted to engage the endplates of upper and lower vertebral bodies V1, V2. The expandable portion 26 is engaged between the end members 22, 24 to maintain an intervertebral axial space S between the upper and lower vertebral bodies V1, V2 following the removal of one or more vertebral levels (shown in phantom). To facilitate insertion of the implant 10, the expandable portion 26 may be collapsed relative to the extended state shown in FIG. 1. For example, FIG. 2A shows the implant 10 in a collapsed state while FIG. 2B shows the implant in an extended state. In FIGS. 2A, 2B, the implant 10 is oriented according to the view lines provided in FIG. 1. Furthermore, the vertebral bodies V1, V2 and other anatomy are omitted for clarity.

The expandable portion 26 is expandable in a direction that is substantially transverse to the bone contact surfaces 32, 34 of the end members 22, 24 as indicated by the arrows labeled X. In one or more embodiments, the implant 10 may be expanded through the introduction of an injectable substance that fills an inflatable balloon-like member 36, thereby causing the end members 22, 24 to move opposite one another. In the embodiment shown in FIGS. 1-5, the expandable portion 26 includes rod portions 38 that extend longitudinally between the end members 22, 24. Crosslink portions 40 extend laterally to interconnect the rod portions 38. In one embodiment, the rod portions 38 and crosslink portions 40 form a single balloon member 36 defining a contiguous internal volume. In other embodiments, the rod portions 38 and some or all of an adjacent crosslink portion 40 are individually inflatable. Furthermore, while FIGS. 1-5 depict four rod portions 38 and two crosslink portions 40, it should be understood that fewer or greater numbers of each portion 38, 40 may be incorporated into the expandable portion 26. It should also be noted that cross links 40 may be rigid or flexible members that are not inflatable. For instance, the rod portions 38 may be tied with cross-links 40 embodied as cables, cords, rings, or tethers.

The balloon-like structure 36 may be constructed of a complaint biocompatible material, such as a resin or polymer that may include materials such as nylon, polyethylene, polyurethane, silicone, polyethylene, polypropylene, polyimide, polyamide, and polyetheretherketone (PEEK). The balloon-like structure 36 may be formed from materials that are used in other conventionally known biomedical applications, such as balloon angioplasty. Further, the balloon-like structure 36 may be reinforced with concentric layers of similar or dissimilar materials and/or fabrics (not specifically shown). For instance, a reinforcing structure may be constructed of a wide variety of woven or nonwoven fibers, fabrics, metal mesh such as woven or braided wires, polymeric fibers, ceramic fibers, and carbon fibers. Biocompatible fabrics or sheet material such as ePTFE and Dacron®, Spectra®, and Kevlar® may also be used.

Various techniques may be used to introduce an injectable substance into the balloon-like structure 36. In the embodiment shown in FIGS. 1-5, a plurality of fill tubes 42 extend from the end members 22, 24. FIG. 4 most clearly shows that the fill tubes 42 provide a duct that is in fluid communication with each of the inflatable rods 38. Each fill tube 42 also includes a coupler 44 that may be attached to a syringe or other pumping mechanism (not shown) to fill the balloon-like structure 36. An injectable substance may flow through the fill tube 42 into the interior volume of the balloon-like structure 36. As the injectable substance fills the balloon-like structure 36, the ends 39 of the rods 38 extend through an aperture 45 and expand to fill an enlarged cavity 46 disposed within the end members 22, 24. As the ends 39 of the rods 38 expand, they exert a displacement force F that causes the end members 22, 24 to separate from one another. Notably, the expanded ends 39 of the rods 38 also operate as anchors that hold the rods 38 within the enlarged cavity 46. Furthermore, the fill tube 42 or the coupler 44 may include a self-sealing valve (not specifically shown) that prevents the injectable substance from flowing in one direction or another once the balloon-like structure 36 is filled.

In the embodiment shown in FIGS. 1-5, a fill tube 42 is disposed at the end of each inflatable rod 38. Therefore, a total of eight fill tubes 42 are provided in the exemplary embodiment. In one implementation, the injectable substance may be introduced into the balloon-like structure 36 through each of these tubes 42. However, in another implementation, one or more of the fill tubes 42 may be used with a vacuum source to pull out the contents of the balloon-like structure 36. Thus, one or more of the fill tubes 42 may be used to introduce the injectable substance while one or more of the fill tubes 42 may be used to vacuum air or other gas out of the balloon-like structure 36 to improve the likelihood that all portions of the various rods 38 or cross-links 40 are filled with the injectable substance. In another implementation, one or more of the fill tubes 42 may be used to introduce the injectable substance while other fill tubes 42 are used as vents that allow air or other gas out of the balloon-like structure 36 as it is filled with the injectable substance.

In another embodiment, fewer fill tubes 42 are used. For instance, a single fill tube 42 may be incorporated in one or both of the end members 22, 24 to permit the introduction of the injectable substance and/or the removal of air or gas from the balloon-like structure 36. However, the remaining rods 38 may be secured with a tether 48 that at least temporarily secures the rod end 39 within the enlarged cavity 46 until the injectable substance is introduced into the balloon-like structure 36.

A variety of injectable substances may be inserted into the balloon-like structure 36 to cause the end members 22, 24 to separate. In one embodiment, the injectable substance is a fluid, such as a gas or a liquid. In one embodiment, the injectable substance is a solid, such as a powder. In one embodiment, the injectable substance is a curable liquid that solidifies after a predetermined amount of time or under the influence of an external catalyst. For instance, an injectable liquid may cure under the influence of heat or light, including ultraviolet light. Some examples of in situ curable liquids include epoxy, PMMA, polyurethane, and silicone. A curable substance may cure to a substantially rigid state or to a flexible, but relatively incompressible state.

Figure 3:
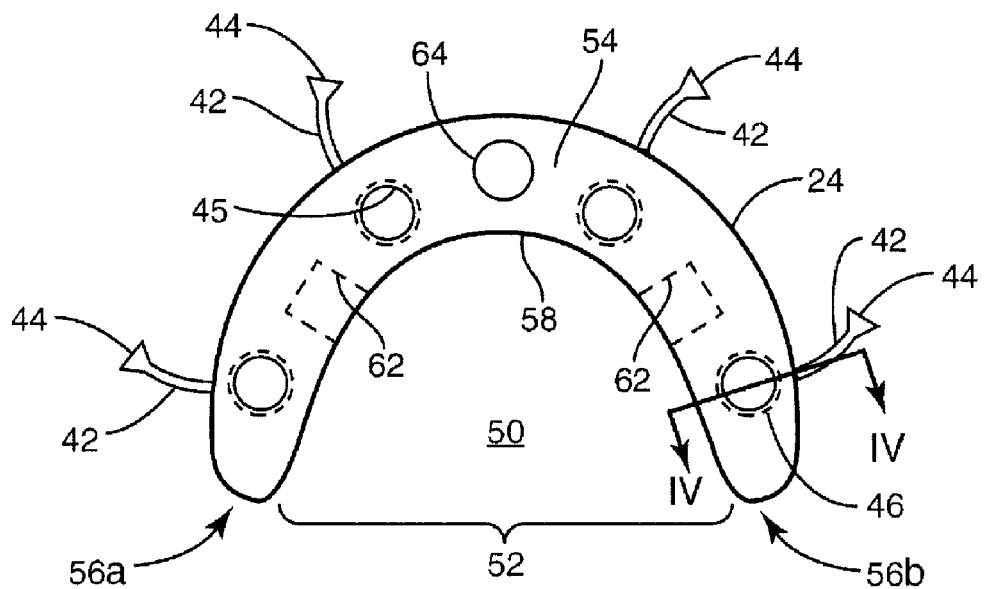
FIG. 3 is a top view of one end portion of a vertebral implant according to one embodiment.
Figure 4:
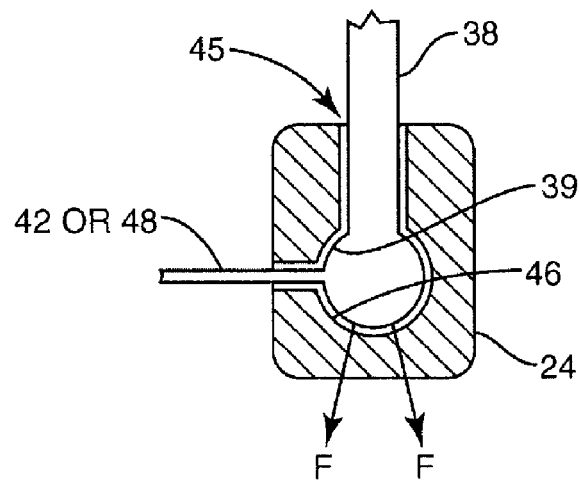
FIG. 4 is partial section view of one end portion of a vertebral implant according to one embodiment.

Referring to FIGS. 2 and 3, shown therein are further details regarding the end members 22, 24. The end members 22, 24 may be configured identical to one another, although the bone contact surfaces 32, 34 (see FIGS. 2A, 2B) may have different contours to match the geometry in vertebral bodies V1, V2. Further, it should be understood that in other embodiments, the end members 22, 24 can take on different configurations.

In one embodiment, each of the end members 22, 24 extends about an open inner region 50 and defining a lateral passage 52. In one embodiment, the end members 22, 24 are generally horseshoe-shaped. In other embodiments, the end members 22, 24 could also be described as being U-shaped, C-shaped, V-shaped, semi-circular shaped, semi-oval shaped, or other terms that could be used to describe a shaped element defining an open inner region 50 and a lateral passage 52 communicating therewith. In further embodiments, the end members 22, 24 may take on other types of hollow configurations, such as, for example, a circular shape, semi-oval shape, bean-shape, kidney shape, D-shape, or any other shape that would occur to one of skill in the art. In still other embodiments, the end members 22, 24 may take on substantially solid configurations, such as, for example, block-like or plate-like configurations that do not define an open inner region.

It should further be appreciated that the size and/or configuration of the end members 22, 24 may be specifically designed to accommodate any particular region of the spinal column and/or any particular vertebral level. For example, in embodiments associated with the upper thoracic or cervical region of the spine, the end members 22, 24 may be designed to have a D-shaped configuration, whereas embodiments associated with the lumbar region of the spine may be configured to have a horseshoe-shape, a U-shape, or other types of open-sided configurations.

Figure 5:
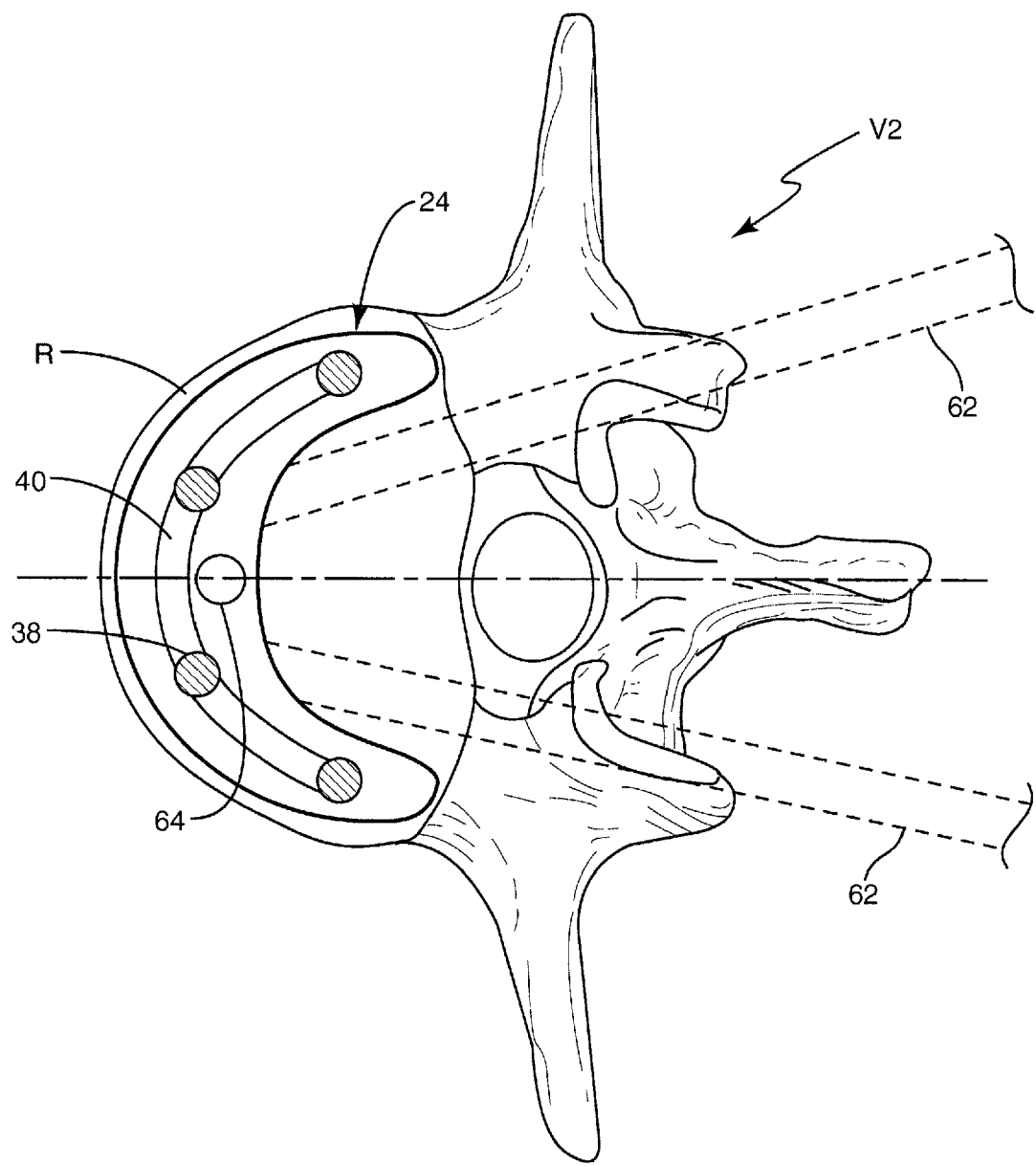
FIG. 5 is a top section view of one end portion of a vertebral implant according to one embodiment.

In one embodiment, the end members 22, 24 have an outer profile that is substantially complementary to the size and shape of the peripheral portion or outlying region of the vertebral bodies V1, V2, such as the cortical rim or the apophyseal ring of the vertebral endplates. For example, as illustrated in FIG. 5, the outer perimeter of the end member 24 is preferably disposed generally above the inner edge of the cortical rim R of the vertebral body V1. In this manner, at least a portion of the end members 22, 24 is engaged against the cortical region of the vertebral endplates, thereby minimizing the likelihood of subsidence into the relatively softer cancellous region of the vertebral bodies V1, V2 following insertion of the implant 10 within the intervertebral space S. Additionally, the open inner region 50 defined by each of the end member 22, 24 provides exposure to the vertebral endplates to enhance bony fusion between the vertebral bodies V1, V2. In one or more implementations, the implant 10 may be inserted in conjunction with bone growth materials that may include, for example, bone graft, bone morphogenetic protein (BMP), allograft, autograft, and various types of cement, growth factors and mineralization proteins. In a further embodiment, the bone growth promoting materials may be provided in a carrier (not shown), such as, for example, a sponge, a block, a cage, folded sheets, or paste.

In the embodiment shown in FIGS. 1-5, the end members 22, 24 include a main body or base portion 54 and a pair of oppositely disposed wings or side portions 56a, 56b extending from the base portion 54. The base portion 54 and the side portions 56a, 56b cooperate to define the open inner region 50, with the distal ends of the side portions 56a, 56b defining the lateral passage 52 therebetween. The lateral surface of the base portion 54 facing the open inner region 50 defines a recessed area 58 that provides for a slightly larger open inner region 30 which correspondingly increases exposure of the vertebral endplates to enhance fusion capabilities.

The bone contact surfaces 32, 34 of the end members 22, 24 may be planar or defines surface features and/or a number of anchor elements adapted for engagement with the vertebral endplates to inhibit movement of the end members 22, 24 relative to the vertebral bodies V1, V2. For example, in one embodiment, the bone contact surfaces 32, 34 may be roughened, such as, for example, by knurling and/or etching (e.g., photochemical etching). In other embodiments, various types of projections or protrusions may extend from the bone contact surfaces 32, 34, such as, for example, a number of spikes, ridges, teeth, axial grooves, checkerboard-type grooves, or any other type of anchoring element that would occur to one of skill in the art. Although the bone contact surfaces 32, 34 of the end members 22, 24 are illustrated in FIGS. 2A, 2B as being arranged substantially parallel to one another, it should be understood that the bone contact surfaces 32, 34 may be tapered relative to one another to more closely conform with the anatomical curvature of the spine at the surgical site (e.g., the angle of lordosis or kyphosis). It should also be understood that the end members 22, 24 may be positioned as desired with a predetermined curvature indicated by the angle G in FIG. 1 to more closely match the configuration of the implant 10 with the anatomical curvature of the spine at the surgical site. Then, in implementations where the injectable substance cures, the expandable portion may solidify in the desired position.

In the illustrated embodiment, the end members 22, 24 each include a laterally-extending aperture 60 that is adapted to receive a corresponding set of elongated rods or posts 62 (shown in phantom). The elongated posts 62 are coupled to the end members 22, 24 and extend outside of the intervertebral space S. In one embodiment, the elongated posts 62 allow a surgeon to position the end members 22, 24 in a desired position, with a desired spacing, and desired sagittal curvature (angle G from FIG. 1) or coronal (arrow C from FIG. 2B) tilt. As suggested above, in implementations where the injectable substance cures, the expandable portion may solidify in the desired position. In other implementations, the apertures 60 may be threaded and may provide an anchoring location for coupling various components to the implant 10 at a location outside of the intervertebral space S. As should be appreciated, various types and configurations of spinal stabilization systems, such as, for example, plate or rod type systems, may be operably attached to the elongated posts 62 to provide additional stability and structural integrity to the implant 10 and/or to provide additional stabilization and support to the portion of the spinal column being treated.

The end members 22, 24 may also include a tool receiving aperture 64. The tool receiving apertures 64 are sized and shaped to receive a corresponding end portion of a tool or instrument (not shown) therein to facilitate insertion of the implant 10 into the intervertebral space S, manipulation of the end members 22, 24, and/or distraction of the intervertebral space S. One example of a tool suited for this purpose as well as various surgical implantation techniques, including a posterior surgical approach that is applicable to the present embodiments, are disclosed in commonly assigned U.S. patent application Ser. No. 10/407,010 (US Patent Application Publication Number 2004/0199252), the contents of which are hereby incorporated by reference herein.

Figure 6:
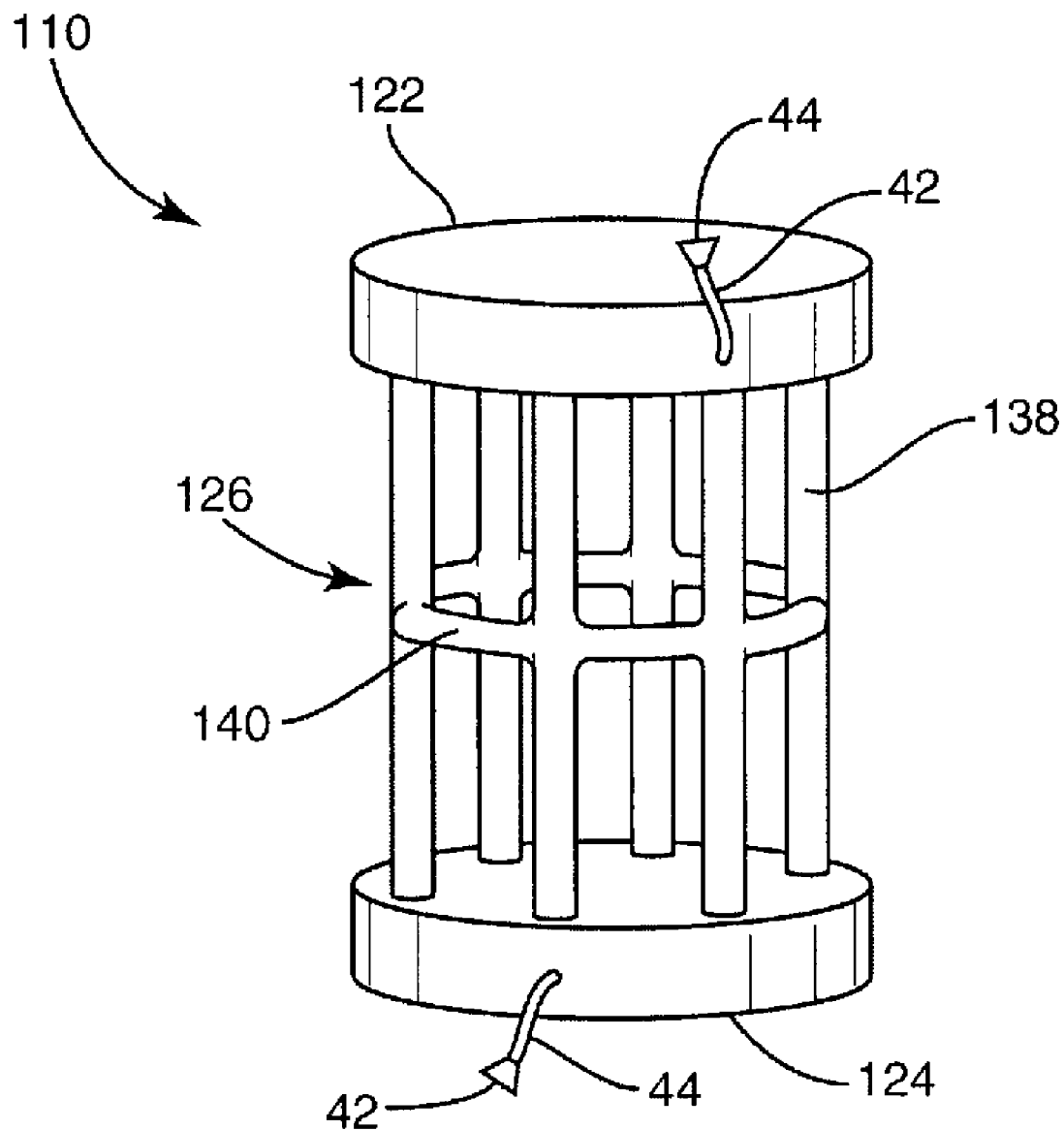
FIG. 6 is a perspective view of a vertebral implant according to one embodiment.

As suggested above, the end members 22, 24 may have other configurations aside from the horseshoe shape depicted in FIGS. 1-5. For instance, the end members 22, 24 may take on substantially solid configurations, such as, for example, block-like or plate-like configurations that do not define an open inner region. FIG. 6 shows an embodiment of an implant 110 where the end members 122, 124 are substantially disc-shaped. This type of implant 110 may be particularly suited to an anterior surgical approach, though posterior or lateral approaches are not precluded. The end members 122, 124 may be substantially circular as depicted or may be constructed with other shapes, including for example, oval, elliptical, trapezoidal, rectangular, or egg-shaped. In this embodiment, the end members 122, 124 are coupled to an expandable portion 126 having a plurality of rods 138 and a single cross-link 140 that transversely couples the rods 138 at a location between the end members 122, 124. The implant 110 shown in FIG. 6 also differs from some of the above described embodiments in that only a single fill tube 42 and associated coupler 44 are included at each end member 122, 124. As described above, these fill tubes 42 may be alternately or simultaneously used for filling, vacuuming, or venting the contents of the expandable portion 126.

Figure 7:
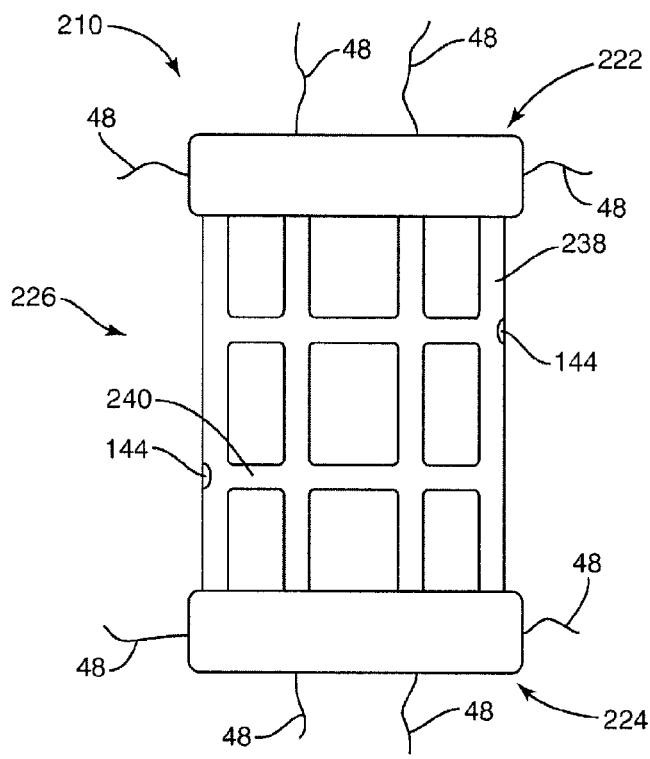
FIG. 7 is a side view of a vertebral implant according to one embodiment.

FIG. 7 illustrates an embodiment of an implant 210 with an expandable portion 226 that includes rods 238 and cross-links 240 as in previously described embodiments. However, implant 210 uses the aforementioned tethers 48 to secure inflatable rod portions 238 to end portions 222, 224. The tethers 48 may be tied off individually or to one another before and after the expandable portion 226 is filled with the injectable substance. In certain implementations where a curable substance is used, the tethers may be cut to a desired length and removed once the injected substance has hardened. The exemplary implant 210 shown in FIG. 7 also includes injection ports 144 that are disposed in the expandable portion 226. The injection ports 144 may include check valves that permit one-way flow of the injectable substance into or out of the expandable portion 226.

Figure 8:
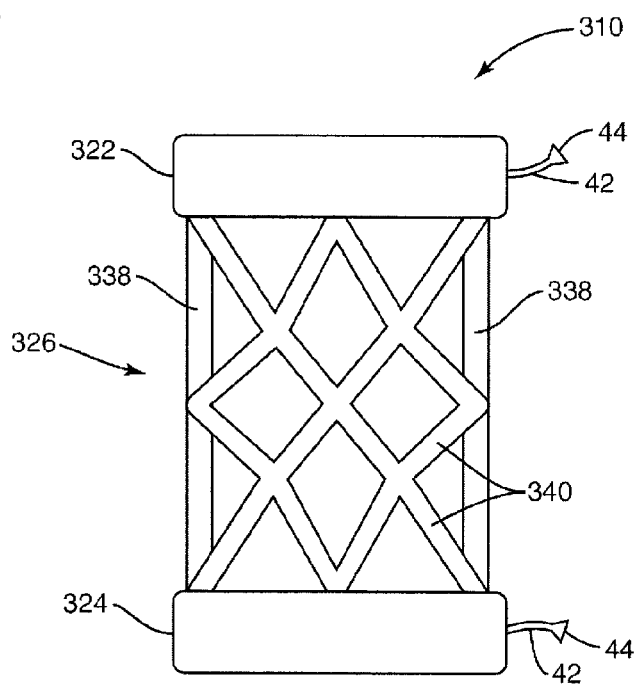
FIG. 8 is a side view of a vertebral implant according to one embodiment.

FIG. 8 illustrates an embodiment of an implant 310 with an expandable portion 326 that interconnects end portions 322, 324. The illustrated expandable portion 326 includes rods 338 and cross-links 340. However, in contrast with previously described embodiments, the cross links 340 are disposed at oblique angles relative to the rods 338.

Figure 9:
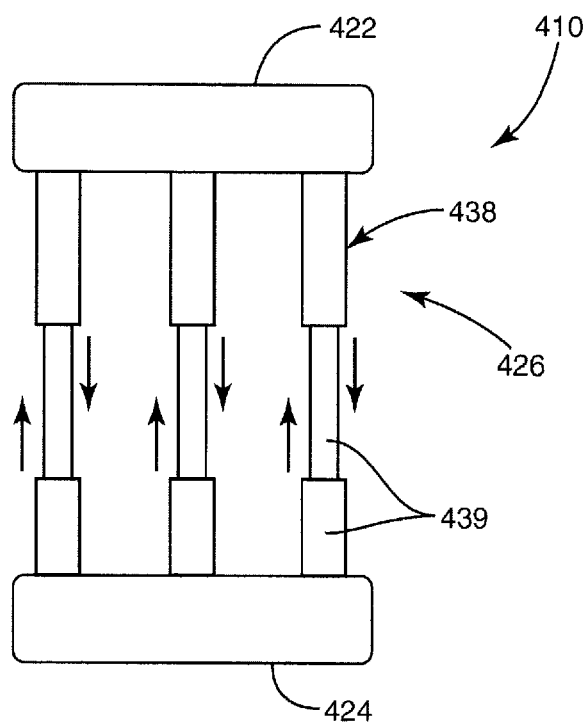
FIG. 9 is a side view of a vertebral implant according to one embodiment.
Figure 10:
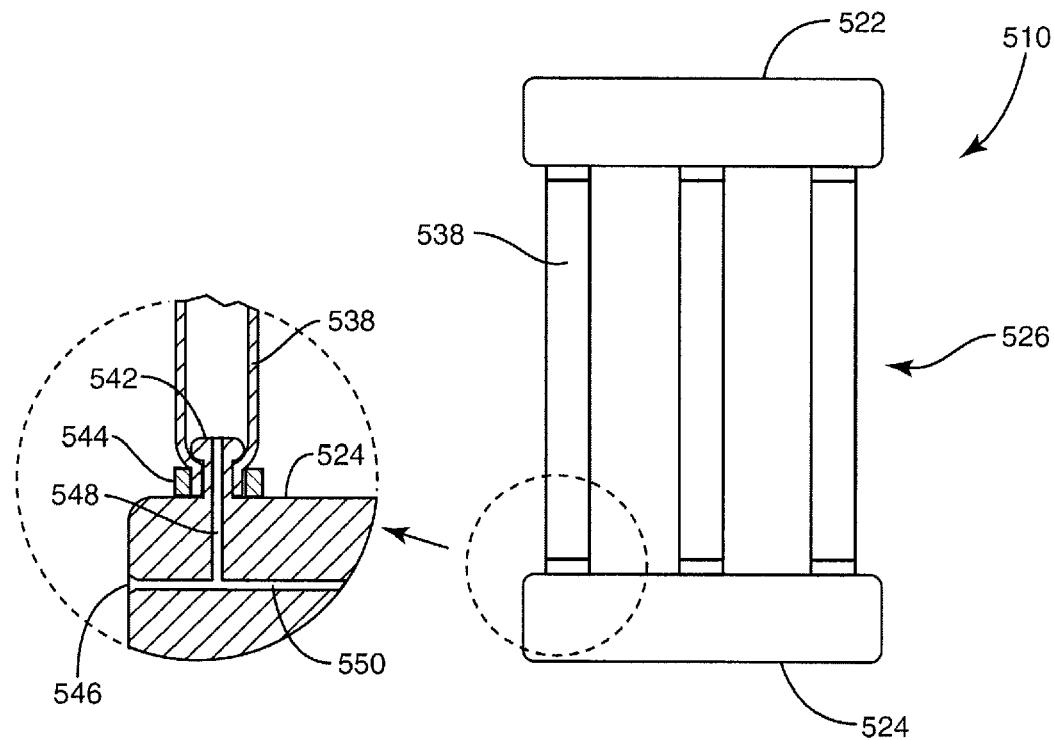
FIG. 10 is a side view, including a partial section detail, of a vertebral implant according to one embodiment.

In contrast, FIGS. 9 and 10 illustrate embodiments of an implant 410, 510 that do not include any cross links. Specifically, FIG. 9 shows an implant 410 that is characterized by a telescoping expandable portion 426 between end portions 422, 424. In contrast with previous embodiments that use a balloon-type design, the illustrated implant 410 has a plurality of rods 438 constructed from a series of concentric columns 439 that are able to collapse within one another in the absence of an injectable material within the expandable portion 426. Upon filling the expandable portion 426 with the injectable material, the concentric columns 439 expand or telescope to the expanded position illustrated in FIG. 9. In one embodiment, the concentric columns 439 are substantially cylindrical. In one embodiment, the concentric columns 439 have a substantially non-circular cross section, including for example, square, oval, star, or polygonal shapes. In one embodiment, the concentric columns 439 are constructed of a substantially rigid biocompatible material. The concentric columns 439 may have seals (not shown) to prevent the injectable substance from escaping once the expandable portion 426 is filled.

FIG. 10 shows an embodiment of an implant 510 in which a plurality of inflatable rods 538 are disposed between end members 522, 524. As with previously described embodiments, the rods 538 are extendable along their longitudinal axis upon the introduction of an injectable substance into the interior of the rods 538. FIG. 10 also provides a detailed section view of the junction between a rod 538 and one of the end members (in this instance, 524). A similar configuration may exist at the opposite end member 522. Specifically, the detailed section view at the left side of FIG. 10 shows a hollow, inflatable rod 538 secured to an anchor 542 that protrudes from the end member 524. The rod 538 is secured to the anchor 542 with a retainer 544. An injectable substance may be introduced to the inflatable rod 538 through an injection port 546 that provides an inlet to an injection manifold 550 that separately feeds the injectable substance into the rods 538 through separate ducts 548. As suggested above, a similar configuration may exist at the opposite end member 522. In one implementation, the injectable substance is inserted into an injection port 546 in both end members 522, 524. In another implementation, the injectable substance is inserted into an injection port 546 in one end member 522 while a vacuum is drawn on the opposite end member to remove air or gas from the rods during the process of expanding the end members 522, 524.

Figure 11:
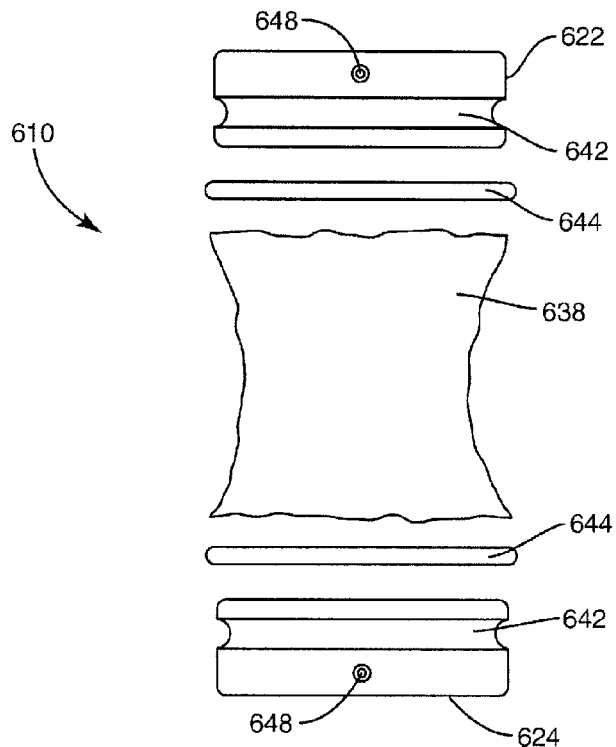
FIG. 11 is a side exploded view of a vertebral implant according to one embodiment.

FIGS. 11, 12, and 13 illustrate an embodiment of an implant 610 that incorporates a single inflatable member 638 as an expandable portion 626 that couples two end portions 622, 624. FIG. 11 shows an exploded side view of the various components making up the present embodiment. The end portions 622, 624 are illustrated as substantially disc-shaped, although other shapes as described herein may be used. An injectable substance may be introduced to the inflatable member 638 through an injection port 648 disposed in end portions 622, 624. As described above, these injection ports 648 may be alternately or simultaneously used for filling, vacuuming, or venting the contents of the expandable member 638.

Each end member 622, 624 includes a recessed groove 642 disposed towards an end that faces the opposite end member 622, 624. The groove 642 is of a shape and depth sufficient to accept a retainer 644. The retainer may be constructed of a biocompatible wire, such as stainless steel or titanium. The inflatable member 638 can be disposed so that it overlaps the circumferential groove 642, and the retainer 644 formed by wrapping a wire around the groove 642 over the overlapping portion of the inflatable member 638, cutting the wire to the appropriate size, and welding the ends of the wire to form a ring. In other embodiments, the retainer 644 may be constructed with a clamping mechanism (not shown) that eliminates the need for welding.

Figures 12A, 12B:
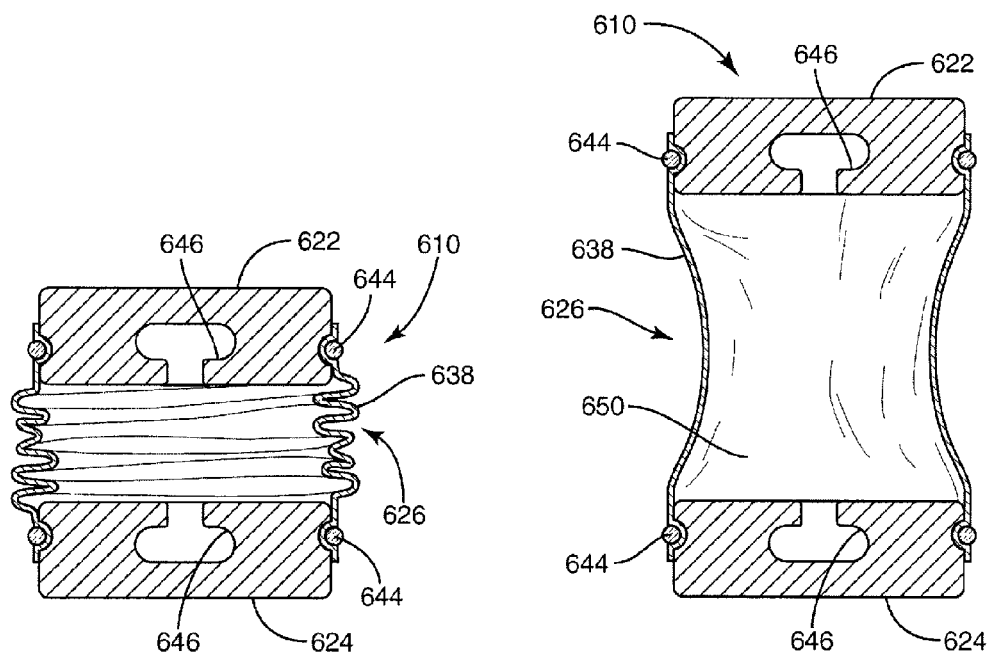
FIG. 12A is a side view of one embodiment of a vertebral implant in a collapsed state.
FIG. 12B is a posterior view of one embodiment of a vertebral implant in an extended state.

FIG. 12A shows a section view of the assembled implant 610 in a collapsed state. By comparison, FIG. 12B shows the same assembled implant 610 in an extended state. As illustrated, the inflatable member 638 is secured to the end portions 622, 624 with the aforementioned retainer 644. The cross section in FIGS. 12A and 12B further illustrates an enlarged cavity 646 in each end portion 622, 624 that is in communication with the interior cavity 650 defined within the inflatable member 638 and between the end portions 622, 624. Thus, as an injectable substance is introduced into the inflatable member 638, the substance also fills the enlarged cavities 646. In certain implementations where a curable substance is used, the enlarged cavities may provide a secure anchoring mechanism adapted at preventing separation of the substance and either of the end members 622, 624.

The various Figures and embodiments disclosed herein have depicted various spinal implant devices that are inserted between or adjacent vertebral bodies. However, the teachings disclosed are certainly applicable to other types of spinal implant devices, including interspinous spacers, interbody cages, arthroplasty devices, and other implants that are coupled to vertebrae V1, V2.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the embodiments disclosed herein have contemplated a single implant positioned between vertebral bodies V1, V2. In other embodiments, two or more smaller implants may be inserted between the vertebral bodies V1, V2. The present embodiments are, therefore, to be considered in all respects as illustrative and not restrictive, and all changes coming within the meaning and equivalency range of the appended claims are intended to be embraced therein.

What is claimed is:

1. A vertebral implant that positions first and second vertebral members within a patient comprising:
    a first end member;
    a second end member;
    an inflatable cage positioned between the first and second end members that includes a port that leads into an enclosed interior space adapted to contain an injectable substance, the cage including a plurality of inflatable rod portions and a plurality of crosslink members;
    the cage positionable between a collapsed state with a first reduced height to facilitate insertion between the first and second vertebral members and an extended state with a second height greater than the first height that positions the first end member against the first vertebral member and the second end member against the second vertebral member to maintain an intervertebral axial space;

in the extended state, the plurality of rod portions extend between the first and second ends members and the plurality of crosslink members extend transverse to the plurality of rod portions, the plurality of rod portions and crosslink members being spaced apart by gaps and exposed within the patient.

2. The vertebral implant of claim 1, wherein the cage includes a contiguous internal volume.

3. The vertebral implant of claim 1, wherein the cage includes at least two individually inflatable sections.

4. The vertebral implant of claim 1, wherein the plurality of crosslink members are perpendicular to the plurality of rod portions.

5. The vertebral implant of claim 1, wherein the port extends through one of the first and second end members.

6. The vertebral implant 1, wherein the first end member includes at least one cavity sized to receive a section of the cage when the cage is in the extended state.

7. A vertebral implant that positions first and second vertebral members comprising:

an inflatable cage with a plurality of longitudinal members;

first and second end members positioned on opposite sides of the cage, each of the end members including a contact side that faces towards one of the first and second vertebral members and an engagement side that faces away from the respective contact side;

each engagement side having a cavity sized to receive an end of one of the plurality of longitudinal members and each of the cavities including a neck and an enlarged receptacle;

the neck of each cavity extending inward into one of the end members from the engagement side and leading into the enlarged receptacle having a greater width than the neck, each neck and enlarged receptacle disposed between the contact side and engagement side of the respective end member;

the cage positionable between a collapsed state with a first reduced height to facilitate insertion between the first and second vertebral members and an extended state with a second height greater than the first height that positions the contact side of the first end member against the first vertebral member and the contact side of the second end member against the second vertebral member to maintain an intervertebral axial space;

when the cage is in the extended state the ends of the plurality of longitudinal members include an enlarged section positioned within the enlarged receptacles, the enlarged sections including a width greater than the neck and less than or equal to the receptacle.

8. The vertebral implant of claim 7, wherein the cage further includes a plurality of crosslink members that are transverse to the plurality of longitudinal members.

9. The vertebral implant of claim 7, wherein the plurality of longitudinal members includes telescoping columns arranged in an overlapping orientation.

10. The vertebral implant of claim 7, further comprising a port that extends through one of the first and second end members and into an interior section of the cage.

11. The vertebral implant of claim 10, further comprising an anchor that extends outward from the engagement side of at least one of the first and second end members and fits within an interior of the end of one of the plurality of longitudinal members.

12. The vertebral implant of claim 11, further comprising a retainer that extends around an exterior of the end of the longitudinal member to maintain the longitudinal member positioned relative to the anchor.

13. A vertebral implant that positions first and second vertebral members comprising:

an inflatable cage;

first and second end members each operatively connected to the cage and positioned on opposite sides of the cage, the end members including a first side that faces towards one of the first and second vertebral members respectively and a second side that faces the cage;

an anchor that extends outward from the second side of one of the end members and into an interior of the cage;

a port that extends through the one end member and through the anchor, the port being in communication with an interior of the cage;

the cage positionable between a collapsed state with a first reduced height to facilitate insertion between the first and second vertebral members and an extended state with a second height greater than the first height that positions the first end member against the first vertebral member and the second end member against the second vertebral member to maintain an intervertebral axial space.

14. The vertebral member of claim 13, further comprising a retainer that extends around an exterior of the cage to maintain the cage attached to the anchor.

15. The vertebral member of claim 13, further comprising a second port positioned on the other end member and in communication with the interior of the cage.

16. The vertebral implant of claim 13, wherein the cage further comprises a plurality of rods that extend between the first and second end members and a plurality of crosslink members that are transverse to the plurality of rods and spaced away from the first and second end members, the plurality of rods and plurality of crosslink members being spaced apart to form gaps therebetween.

17. The vertebral implant of claim 13, wherein the cage further comprises a plurality of longitudinal members with telescoping columns arranged in an overlapping orientation.

18. The vertebral implant of claim 13, wherein the cage includes a contiguous internal volume.

19. The vertebral implant of claim 13, wherein the cage includes at least two individually inflatable sections.

* * * * *